US010975021B2

(12) United States Patent
Lee et al.

(10) Patent No.: US 10,975,021 B2
(45) Date of Patent: Apr. 13, 2021

(54) METHOD FOR PREPARING ALIPHATIC ISOCYANATE

(71) Applicant: Hanwha Solutions Corporation, Seoul (KR)

(72) Inventors: Byeong Hyeon Lee, Seoul (KR); Ju Young Park, Suwon-si (KR); Cho Hee Ahn, Seoul (KR); Sang Hyun Cho, Anyang-si (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

(21) Appl. No.: 16/642,996

(22) PCT Filed: Sep. 3, 2018

(86) PCT No.: PCT/KR2018/010227
§ 371 (c)(1),
(2) Date: Feb. 28, 2020

(87) PCT Pub. No.: WO2019/050236
PCT Pub. Date: Mar. 14, 2019

(65) Prior Publication Data
US 2020/0190022 A1   Jun. 18, 2020

(30) Foreign Application Priority Data
Sep. 11, 2017   (KR) .......................... 10-2017-0116138

(51) Int. Cl.
*C07C 263/10*   (2006.01)
*C07C 263/04*   (2006.01)
C07C 265/08   (2006.01)
C07C 265/12   (2006.01)

(52) U.S. Cl.
CPC .......... *C07C 263/10* (2013.01); *C07C 263/04* (2013.01); *C07C 265/08* (2013.01); *C07C 265/12* (2013.01)

(58) Field of Classification Search
CPC ... C07C 263/00; C07C 263/10; C07C 265/04; C07C 265/08; C07C 265/12; C07C 263/04
See application file for complete search history.

(56) References Cited

U.S. PATENT DOCUMENTS

| 3,188,337 A * | 6/1965 | Gemassmer .......... C07C 263/04 560/347 |
| 3,234,253 A | 2/1966 | Cooper |
| 3,574,695 A * | 4/1971 | Grant .................... C07C 265/14 560/347 |
| 5,523,467 A * | 6/1996 | Okazaki ................ C07C 263/10 560/347 |
| 5,679,839 A | 10/1997 | Armand et al. |
| 7,211,689 B2 * | 5/2007 | Rohde ................... C07C 263/10 560/338 |

FOREIGN PATENT DOCUMENTS

| CN | 102070491 A | * 5/2011 | .......... C07C 263/10 |
| EP | 0424836 | 3/1995 | |
| JP | 60-255756 | 12/1985 | |
| JP | 03-220167 | 9/1991 | |
| JP | 07-309827 | 11/1995 | |
| JP | H07-309827 A | * 11/1995 | .......... C07C 263/10 |
| JP | 2007-051092 | 3/2007 | |
| KR | 10-1994-0001948 | 3/1994 | |
| KR | 10-1996-0007551 | 3/1996 | |
| KR | 10-2004-0011808 | 2/2004 | |
| KR | 10-1232431 | 2/2013 | |

OTHER PUBLICATIONS

CN 102070491, Jiansheng Ding, et al, Mehod for preparing xylylene diisocynanate based on salification-phosgenatin reaction, English translation 12 pages (Year: 2011).*
KIPO, PCT Search Report & Written Opinion of PCT/KR2018/010227 dated Dec. 12, 2018.
JPO, Office Action of JP 2020-515555 dated Mar. 1, 2021.

* cited by examiner

*Primary Examiner* — Yate' K Cutliff
(74) *Attorney, Agent, or Firm* — Lex IP Meister, PLLC

(57) ABSTRACT

The present invention relates to a method for preparing an aliphatic isocyanate capable of suppressing the occurrence of side reactions and the production of by-products. The method for preparing an aliphatic isocyanate comprises a step of reacting a salt of an aliphatic amine with phosgene, wherein the reaction step comprises a first reaction step in which phosgene is primarily added and reacted with the salt of an aliphatic amine salt at a temperature of 80 to 100° C., and a second reaction step in which phosgene is secondarily added and reacted with the resultant product of the first reaction step at a temperature of 120 to 160° C., and wherein the amount of the primarily added phosgene is a certain ratio of the total amount of the phosgene.

9 Claims, No Drawings

METHOD FOR PREPARING ALIPHATIC ISOCYANATE

CROSS-REFERENCE TO RELATED APPLICATION(S)

This application claims the benefits of filing date of Korean Patent Application No. 10-2017-0116138 filed with Korean Intellectual Property Office on Sep. 11, 2017, the entire content of which is incorporated herein by reference.

The present invention relates to a method for preparing an aliphatic isocyanate with high purity, more specifically, to a method for preparing an aliphatic isocyanate with high purity comprising an aliphatic polyisocyanate capable of suppressing the occurrence of side reactions and the production of by-products.

TECHNICAL FIELD

Background

Xylylene diisocyanate (hereinafter referred to as XDI) includes an aromatic ring, but it is classified as a member of aliphatic isocyanates, and is a very useful compound as raw materials such as a polyurethane-based material, a polyurea-based material, a polyisocyanurate-based material and the like in the fields of chemical industry, resin industry and paint industry.

Generally, aliphatic isocyanates are produced by a method in which many side reactions occur during synthesis and a salt is formed through reaction with anhydrous hydrochloric acid or carbonic acid, and reacted with phosgene. As an example, in the case of XDI, it is produced by reacting xylylene diamine (hereinafter referred to as XDA) with anhydrous hydrochloric acid to form an amine-hydrochloride salt, and then reacting this salt with phosgene. More specifically, conventionally, a method for preparing an aliphatic isocyanate such as XDI through the steps of reacting liquid raw material amines, for example, an XDA-containing solution, with anhydrous hydrochloric acid to form an XDA-HCl hydrochloride, heating the hydrochloride to a high temperature of at least 100° C. and then adding gaseous phosgene thereto to carry out a gas-liquid reaction has been employed.

The reason why the reaction proceeded under high-temperature heating in this manner is that in particular, the formation reaction of the aliphatic isocyanate is a typical endothermic reaction, and continuous heating and high-temperature maintenance during the reaction are required to increase the yield thereof.

However, the aliphatic isocyanates such as XDI generally have a large reactivity of amino groups, and so many side reactions occur during the phosgenation reaction. The impurities formed through side reactions affect the reaction of forming the polyurethane resin, which cause a problem that the quality of the resin is deteriorated.

Due to the necessity of maintaining a high temperature during the production process of the aliphatic isocyanate as described above, and the large reactivity of the produced aliphatic isocyanate such as XDI, there were disadvantages that the possibility of the formation of by-products and the occurrence of side reactions due to thermal denaturation or the like of the product are further increased, so that a large load often occurred even in the purification process.

Due to these problems, previously, several attempts have been made to suppress side reactions during the preparation of aliphatic isocyanate and the formation of by-products, but no effective technology has been developed yet. In addition, there was a disadvantage that an explosive vaporization of phosgene occurs during the above-described manufacturing process and thus the risk is higher.

TECHNICAL PROBLEM

The present invention provides a method for preparing an aliphatic isocyanate with high purity, which can suppress the occurrence of side reactions or the formation of by-products as the reaction steps are progressed sequentially during the preparation of an aliphatic isocyanate using phosgene.

TECHNICAL SOLUTION

The present invention provides a method for preparing an aliphatic isocyanate comprising a step of reacting a salt of an aliphatic amine with phosgene, wherein the reaction step comprises a first reaction step in which phosgene is primarily added and reacted with the salt of an aliphatic amine at a temperature of 80 to 100° C., and a second reaction step in which phosgene is secondarily added and reacted with the resultant product of the first reaction step at a temperature of 120 to 160° C., and wherein the amount of the primarily added phosgene is 10 to 30% by weight of the total amount of the primarily and secondarily added phosgene.

ADVANTAGEOUS EFFECTS

According to the preparation method of the present invention, it is possible to minimize the occurrence of side reactions and the formation of by-products, and thus to produce a high purity aliphatic isocyanate in a high yield through a simple preparation process. In addition, the high-temperature reaction time of phosgene is relatively shortened, and the risk of explosive vaporization of phosgene can also be greatly reduced.

DETAILED DESCRIPTION OF THE EMBODIMENTS

Terms used herein are used only to describe particular embodiments only and is not intended to be limiting of the invention. The singular expressions are intended to include plural expressions as well, unless the context clearly indicates otherwise. It should be understood that the terms "comprise," "include", "have", etc. are used herein to specify the presence of stated features, numbers, steps, components or combinations thereof, but do not preclude the presence or addition of one or more other features, numbers, steps, components, or combinations thereof.

Since the embodiments of the present invention are susceptible to various modifications and alternative forms, specific embodiments thereof will be illustrated and described in detail below. It should be understood, however, that the present invention is not limited to the particular embodiments disclosed, but on the contrary, the invention is to cover all modifications, equivalents, and alternatives falling within the spirit and scope of the invention.

According to one embodiment of the present invention, there is provided a method for preparing an aliphatic isocyanate comprising a step of reacting an aliphatic amine salt with phosgene, wherein the reaction step comprises a first reaction step in which phosgene is primarily added and reacted with the aliphatic amine salt at a temperature of 80 to 100° C., and a second reaction step in which phosgene is secondarily added and reacted with the resultant product of the first reaction step at a temperature of 120 to 160° C., and wherein the amount of the primarily added phosgene is 10 to 30% by weight of the total amount of the primarily and secondarily added phosgene.

Generally, the preparation of an aliphatic isocyanate is carried out by the reaction of an aliphatic amine and phosgene. At this time, a side reaction occurs, and as a side reaction product, for example, a monoisocyanate such as chloromethylbenzyl isocyanate (CMBI) is produced. The occurrence of such side reactions and the formation of by-products are known to be caused by the necessity of maintaining a high temperature during the preparation of an aliphatic isocyanate and the large reactivity of the produced aliphatic isocyanate such as XDI. In particular, when the aliphatic isocyanate as the final product is exposed to a high temperature for a certain period of time, it causes side reactions and can form polymeric by-products, such as oligomers or polymers containing dimers, trimers or higher multimers.

In the preparation method of one embodiment, in order to suppress the generation of such side reactions and/or by-products, phosgene is primarily added in a relatively small amount at a relatively low temperature to produce an intermediate, and then while secondarily adding a residual amount of phosgene, the phosgene and the intermediate can reacted to form an aliphatic isocyanate.

As an example, in the case of xylylene diisocyanate (XDI) belonging to aliphatic isocyanate, it is formed by the reaction of xylylene diamine and phosgene. In the first reaction step, while primarily adding the small amount of phosgene, the phosgene is reacted with a salt of xylylenediamine at a relatively low temperature, thereby producing an intermediate in the form of carbamoyl salts. In particular, at this time, in order to appropriately form the intermediate by reacting at a relatively low rate, it is prepared in advance in the form of a salt of an aliphatic amine such as xylylenediamine and allowed to react.

Subsequently, while the remaining amount of phosgene is secondarily added at a high temperature, such phosgene can be reacted with an intermediate in the form of the carbamoyl salt to form an aliphatic isocyanate such as xylylene diisocyanate.

According to the method of this embodiment, the time during which the aliphatic isocyanate as a final product is exposed to high temperature heat can be minimized, and further, as an intermediate is formed in the first reaction step at a relatively low temperature, it is possible to reduce the time required for maintaining the high temperature in the overall reaction process. As a result, the occurrence of side reactions or the production of by-products can be greatly reduced during the process of producing the aliphatic isocyanate.

In addition, as the amount of heat added to the overall process decreases, the overall process cost can also be reduced.

Therefore, according to the preparation method of one embodiment, a high purity aliphatic isocyanate can be produced in a high yield through a simple preparation process. Furthermore, the high temperature reaction time of phosgene is relatively shortened, and thus the risk of explosive vaporization of phosgene can also be greatly reduced.

Hereinafter, the preparation method of one embodiment will be described for each step.

In the method of one embodiment, first, a first reaction step of reacting phosgene with the salt of an aliphatic amine while primarily adding phosgene at a temperature of 80 to 100° C., or 85 to 95° C. is carried out.

The aliphatic amine which can be used is not particularly limited as long as it is an amine having an aliphatic group. Specifically, the aliphatic amine may be a chain or cyclic aliphatic amine, and more specifically, it may be a bifunctional or more chain or cyclic aliphatic amine containing two or more amino groups in the molecule. Specific examples thereof include hexamethylenediamine, 2,2-dimethylpentanediamine, 2,2,4-trimethylhexanediamine, butenediamine, 1,3-butadiene-1,4-diamine, 2,4,4-trimethylhexamethylenediamine, 1,6,11-undecatriamine, 1,3,6-hexamethylenetriamine, 1,8-diisocyanato-4-isocyanatomethyloctane, bis(aminoethyl)carbonate, bis(aminoethyl)ether, xylylenediamine, α,α,α',α'-tetramethyl xylylenediamine, bis(aminoethyl)phthalate, bis(aminomethyl)cyclohexane, dicyclohexylmethane diamine, cyclohexanediamine, methylcyclohexanediamine, dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl) tricyclodecane, bis(aminomethyl) norbornene, or the like. Any one or a mixture of two or more of them may be used. On the other hand, in one embodiment of the invention, xylylenediamine is classified as a member of aliphatic diamines.

Further, as the aliphatic amine, sulfur-containing aliphatic amines such as bis(aminomethyl)sulfide, bis(aminoethyl) sulfide, bis(aminopropyl)sulfide, bis(aminohexyl)sulfide, bis(aminomethyl)sulfone, bis(aminomethyl)disulfide, bis (aminoethyl)disulfide, bis(aminopropyl)disulfide, bis(aminomethylthio)methane, bis(aminoethylthio)methane, bis (aminoethylthio) ethane, bis(aminomethylthio)ethane, 1,5-diamino-2-aminomethyl-3-thiapentane, or the like may be used.

Among the aliphatic amines, xylylenediamine or a salt thereof may exhibit superior effects when applied to a method for preparing an aliphatic isocyanate according to one embodiment of the present invention. Specifically, it may be xylylene diamine (XDA) such as m-xylylene diamine, p-xylylene diamine or o-xylylene diamine, XDA-HCl salt, XDA carbonate, or the like, and one or more of these compounds may be used.

Meanwhile, in the method of one embodiment including the first reaction step, in order to suppress the rapid reaction with phosgene, rather than the aliphatic amine being used by itself, for example, a salt of an aliphatic amine such as a hydrochloride or a carbonate of an aliphatic amine in a solid state is used. The salt of an aliphatic amine may be prepared in advance by a neutralization reaction by reacting the aliphatic amine with anhydrous hydrochloric acid or carbonic acid before the first reaction step. The neutralization reaction for the salt formation may be carried out at a temperature equivalent to or lower than the first reaction step. For example, such a neutralization reaction may be carried out at a temperature of 20 to 80° C.

As a result, the overall reaction steps including the first reaction step are carried out by a three-phase reaction of gas-liquid-solid in which a solid state aliphatic amine salt reacts with a gaseous phosgene in a liquid medium of an organic solvent described hereinafter. Thereby, the rapid reaction can be further suppressed, and thus the occurrence of by-products/side reactions can be further suppressed.

In addition, the overall reaction steps including the first reaction step may be carried out in an organic solvent having a boiling point of 120° C. or higher, more specifically 120 to 200° C. When carried out in a solvent having such a high boiling point, a high purity aliphatic isocyanate can be produced in high yield.

Further, the organic solvent may include at least one of an aromatic hydrocarbon-based organic solvent and an ester-based organic solvent.

The aromatic hydrocarbon-based organic solvent may be specifically a halogenated aromatic hydrocarbon-based organic solvent such as monochlorobenzene, 1,2-dichlorobenzene, or 1,2,4-trichlorobenzene.

Further, specific examples of the ester-based organic solvent include fatty acid esters such as amyl formate, n-butyl acetate, isobutyl acetate, n-amyl acetate, isoamyl acetate, methyl isoamyl acetate, methoxybutyl acetate, sec-hexyl acetate, 2-ethylbutyl acetate, 2-ethylhexyl acetate, cyclohexyl acetate, methylcyclohexyl acetate, benzyl acetate, ethyl propionate, n-butyl propionate, isoamyl propionate, ethyl acetate, butyl stearate, butyl lactate or amyl lactate; and aromatic carboxylic acid esters such as methyl salicylate, dimethyl phthalate or methyl benzoate.

More specifically, the organic solvent may, among the above-mentioned aromatic hydrocarbon-based organic solvent and ester-based organic solvent, include at least one of an aromatic hydrocarbon-based organic solvent and an ester-based organic solvent having a boiling point of 120° C. or higher, or 120° C. to 200° C.

When the phosgenation reaction is carried out in the organic solvent in this way, the salt of an aliphatic amine may be used in a concentration of 20% by volume or less. When the concentration of the aliphatic amine or its salt exceeds 20% by volume, a large amount of amine hydrochloride may be precipitated.

On the other hand, the first reaction step using each of the reactants described above can be carried out at a temperature of 80 to 100° C., more specifically 85 to 95° C., and the amount of phosgene added in the first reaction step may be 10 to 30% by weight, or 12 to 30% by weight, or 15 to 28% by weight, based on the total amount of phosgene added in the first and second reaction steps. Depending on these reaction conditions, the rapid reaction is suppressed in the first reaction step, and intermediates of the carbamoyl salt type can be selectively and effectively formed.

Meanwhile, after the above-mentioned first reaction step, while secondarily adding 70 to 90% by weight, or 70 to 85% by weight, or 72 to 80% by weight of phosgene based on the amount added and remained in the first reaction step, for example, the total amount of phosgene added in the first and second reaction steps, the second reaction step of reacting the phosgene with the resultant product of the first reaction step, that is, an intermediate in the form of the carbamoyl salt at a temperature of 120 to 160° C., more specifically 125 to 145° C. may be carried out.

Such a second reaction step can be carried out according to the same methods and conditions as those of the first reaction step except for the reaction temperature and the amount of the phosgene to be added, and therefore, an additional explanation thereof will be omitted.

Further, the overall reaction steps including the above-described first and second reaction steps can be continuously carried out in a reaction apparatus including: a reactor having a rotation axis; a reactant supply unit connected to the inside of the reactor; a heat source for supplying heat to the reactor; and a product collecting unit for collecting reactants produced in the reactor.

Meanwhile, after completion of each reaction step, a removal step such as nitrogen bubbling with respect to unreacted phosgene or the like, and a solvent removal step through distillation or the like can be selectively carried out. These steps can be carried out according to a conventional method.

The preparation method of one embodiment described above is suitable for the preparation of an isocyanate including a common aliphatic isocyanate or aliphatic polyisocyanate. Specifically, it is useful for the preparation of n-pentyl isocyanate, 6-methyl-2-heptane isocyanate, cyclopentyl isocyanate, hexamethylene diisocyanate (HDI), isophorone diisocyanate (IPDI), diisocyanatomethylcyclohexane (H6TDI), xylylene diisocyanate (XDI), diisocyanatocyclohexane (t-CHDI) or di(isocyanatocyclohexyl)methane (H12MDI), and the like. In particular, it may be more useful for the preparation of xylylene diisocyanate (XDI).

In the method of one embodiment as described above, the time during which the aliphatic isocyanate as a final product is exposed to high-temperature heat can be minimized by the gradual progress of the above-mentioned first and second reaction steps. Further, as an intermediate is formed in the first reaction step at a relatively low temperature, it is possible to reduce the time required for maintaining the high temperature in the overall reaction steps. As a result, the occurrence of side reactions or the formation of by-products can be greatly reduced during the production of the aliphatic isocyanate.

In addition, as each of the above reaction steps, particularly the first reaction step, is carried out in a three-phase reaction of gas-liquid-solid of reacting a solid state aliphatic amine salt with gaseous phosgene in a liquid medium of an organic solvent, the rapid reaction can be further suppressed, and thus the occurrence of by-products/side reactions can be further suppressed.

Furthermore, the high temperature reaction time of phosgene is relatively shortened, and thus the risk of explosive vaporization of phosgene can be greatly reduced.

EXAMPLES

Hereinafter, the function and effect of the present invention will be described in more detail through specific examples of the invention. It is to be understood, however, that these examples are merely illustrative of the invention and are not intended to limit the scope of the invention.

[Analysis]

The phosgene reaction products were analyzed using GC. The GC used for the analysis was HP-6890, which was detected by FID. The column used was DB-17 (30 m*0.25 mm*0.5 μm), the carrier gas was nitrogen (1.0 mL/min), and the oven temperature was 80° C.→5° C./min→160° C. (8 min)→20° C./min→280° C. (18 min).

Example 1

First, 17.5 g of hydrochloric acid and 32.5 g of xylylenediamine (XDA) were reacted in 471.5 g of 1,2-dichlorobenzene solvent under normal temperature and pressure conditions to form 50.0 g of xylylenediamine hydrochloride.

In a state where the temperature of the flask containing 50.0 g of the xylenediamine hydrochloride was raised to 60° C. and maintained, 9.0 g of phosgene was added to the reactor and stirred. It was set to prevent phosgene from leaking to the outside using a dry ice-acetone condenser from the point of addition of phosgene to the end point of the reaction. The reaction was allowed to proceed at a temperature of 90° C. for 1.5 hours.

Subsequently, the inside temperature of the flask was heated to 125° C., and 51.0 g of phosgene was further added using a dropping funnel. The temperature of the flask was set to maintain at 125° C., and the reaction solution was further stirred for 4.5 hours until it became transparent. When the reaction solution became transparent, the heating was stopped, and cooled to 80° C., and then bubbling of nitrogen was carried out. The resulting reaction solution was recovered and 1,2-dichlorobenzene was removed via vacuum distillation, and the analysis was carried out by GC. The analysis results are shown in Table 1 below.

Example 2

First, 17.5 g of hydrochloric acid and 32.5 g of xylylenediamine (XDA) were reacted in 471.5 g of 1,2-dichlorobenzene solvent under normal temperature and pressure conditions to form 50.0 g of xylylenediamine hydrochloride.

In a state where the temperature of the flask containing 50.0 g of the xylenediamine hydrochloride was raised to 60° C. and maintained, 15.0 g of phosgene was added to the reactor and stirred. It was set to prevent phosgene from leaking to the outside using a dry ice-acetone condenser from the point of addition of phosgene to the end point of the reaction. The reaction was allowed to proceed at a temperature of 90° C. for 1.5 hours.

Subsequently, the inside temperature of the flask was heated to 125° C., and 45.0 g of phosgene was further added using a dropping funnel. The temperature of the flask was set to maintain at 125° C., and the reaction solution was further stirred for 4 hours until it became transparent. When the reaction solution became transparent, the heating was stopped, and cooled to 80° C., and then bubbling of nitrogen was carried out. The resulting reaction solution was recovered and 1,2-dichlorobenzene was removed via vacuum distillation, and the analysis was carried out by GC. The analysis results are shown in Table 1 below.

Comparative Example 1

First, 17.5 g of hydrochloric acid and 32.5 g of xylylenediamine (XDA) were reacted in 471.5 g of 1,2-dichlorobenzene solvent under normal temperature and pressure conditions to form 50.0 g of xylylenediamine hydrochloride.

In a state where the temperature of the flask containing 50.0 g of the xylenediamine hydrochloride was raised to 120° C. and maintained, 60 g of phosgene was added to the reactor and stirred. It was set to prevent phosgene from leaking to the outside using a dry ice-acetone condenser from the point of addition of phosgene to the end point of the reaction. The temperature of the flask was set to maintain at 125° C., and the reaction was proceeded while stirring the reaction solution for 8 hours until it became transparent. When the reaction solution became transparent, the heating was stopped, and cooled to 80° C., and then bubbling of nitrogen was carried out. The resulting reaction solution was recovered and 1,2-dichlorobenzene was removed via vacuum distillation, and the analysis was carried out by GC. The analysis results are shown in Table 1 below.

Comparative Example 2

First, 17.5 g of hydrochloric acid and 32.5 g of xylylenediamine (XDA) were reacted in 471.5 g of 1,2-dichlorobenzene solvent under normal temperature and pressure conditions to form 50.0 g of xylylenediamine hydrochloride.

While the temperature of the flask containing 50.0 g of the xylenediamine hydrochloride was rapidly raised to 125° C. from the initial temperature of 25° C. (R.T. level), 60 g of phosgene was slowly added to the reactor over 7 hours and stirred. It was set to prevent phosgene from leaking to the outside using a dry ice-acetone condenser from the point of addition of phosgene to the end point of the reaction.

While proceeding the reaction for 14 hours in this way, the reaction solution was stirred until it became transparent. When the reaction solution became transparent, the heating was stopped, and cooled to 80° C., and then bubbling of nitrogen was carried out. The resulting reaction solution was recovered and 1,2-dichlorobenzene was removed via vacuum distillation, and the analysis was carried out by GC. The analysis results are shown in Table 1 below.

TABLE 1

| | | Example 1 | Example 2 | Comparative Example 1 | Comparative Example 2 |
|---|---|---|---|---|---|
| Reaction condition | | After a first reaction at 90° C., a second reaction at 125° C. | After a first reaction at 90° C., a second reaction at 125° C. | Reacted while adding phosgene at 125° C. | Reacted by continuously adding phosgene while raising the temperature to 125° C. |
| Total reaction time | | 6 hours (1.5 hr + 4.5 hr) | 6 hours (2 hr + 4 hr) | 8 hours | 7 hours |
| XDI purity (%)*[1] | | 99.102 | 99.111 | 98.504 | 98.717 |
| Monoisocyanate content (%)*[1] | EBI*[2] | 0.087 | 0.084 | 0.263 | 0.171 |
| | CMBI*[3] | 0.54 | 0.56 | 1.032 | 0.76 |
| | Other*[4] | 0.154 | 0.155 | 0.089 | 0.136 |

*[1] area % during GC analysis
*[2] EBI(Ethylbenzylisocyanate), RT: 9.18 min
*[3] CMBI(Chloromethylbenzylisocyanate), RT: 10.01 min
*[4] Not defined, RT: 16.5~24.9 min From the above experimental results, it was confirmed that during the preparation of aliphatic isocyanate using phosgene, as the multistage reactions proceeded as in Examples 1 and 2, the content of impurities such as monoisocyanate and the like can be lowered and a high purity aliphatic isocyanate can be produced.

In Comparative Examples 1 and 2, it was confirmed to be difficult to obtain aliphatic isocyanate with sufficiently high purity.

The invention claimed is:

1. A method for preparing an aliphatic isocyanate comprising a step of reacting a salt of aliphatic amine with phosgene,
wherein the reaction step comprises a first reaction step in which phosgene is primarily added and reacted with the salt of an aliphatic amine at a temperature of 80 to 100° C., and a second reaction step in which phosgene is secondarily added and reacted with the resultant product of the first reaction step at a temperature of 120 to 160° C., and
wherein the amount of the primarily added phosgene is 10 to 30% by weight of the total amount of the primarily and secondarily added phosgene.

2. The method for preparing an aliphatic isocyanate according to claim 1, wherein the salt of an aliphatic amine includes a hydrochloride or a carbonate of an aliphatic amine in a solid state.

3. The method for preparing an aliphatic isocyanate according to claim 1, further comprising a step of reacting the aliphatic amine with hydrochloric acid or carbonic acid before the first reaction step to form a salt of an aliphatic amine in a solid state.

4. The method for preparing an aliphatic isocyanate according to claim 1, wherein the reaction step is carried out in an organic solvent having a boiling point of 120° C. or higher.

5. The method for preparing an aliphatic isocyanate according to claim 1, wherein the reaction step is carried out in an organic solvent selected from the group consisting of an aromatic hydrocarbon-based organic solvent, an ester-based organic solvent and a mixture thereof.

6. The method for preparing an aliphatic isocyanate according to claim 4, wherein the reaction step is carried out by a three-phase reaction of gas-liquid-solid in which a salt of an aliphatic amine in the solid state reacts with a gaseous phosgene in a liquid medium of the organic solvent.

7. The method for preparing an aliphatic isocyanate according to claim 1, wherein a carbamoyl-based intermediate is formed in the first reaction step.

8. The method for preparing an aliphatic isocyanate according to claim 1, wherein the aliphatic amine is xylylene diamine.

9. The method for preparing an aliphatic isocyanate according to claim 1, wherein the reaction step is carried out in a reaction apparatus comprising: a reactor having a rotation axis; a reactant supply unit connected to the inside of the reactor; a heat source for supplying heat to the reactor; and a product collecting unit for collecting reactants produced in the reactor.

* * * * *